US00PP26543P2

(12) United States Plant Patent
Wood

(10) Patent No.: US PP26,543 P2
(45) Date of Patent: Mar. 29, 2016

(54) *CEPHALANTHUS* PLANT NAMED 'SMCOSS'

(50) Latin Name: *Cephalanthus occidentalis*
Varietal Denomination: SMCOSS

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 116 days.

(21) Appl. No.: 13/998,228

(22) Filed: Oct. 15, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — C. A. Whealy

(57) ABSTRACT

A new and distinct cultivar of *Cephalanthus* plant named 'SMCOSS', characterized by its compact, upright and mounded plant habit; vigorous growth habit; freely branching habit; dense and bushy habit; glossy green-colored leaves that develop anthocyanin in the spring and autumn; spherical head-type inflorescences with numerous white-colored flowers; red-colored fruits; and good garden performance.

3 Drawing Sheets

Botanical designation: *Cephalanthus occidentalis*.
Cultivar denomination: 'SMCOSS'.

BACKGROUND OF THE INVENTION

The present invention relates to a new and distinct *Cephalanthus* plant, botanically known as *Cephalanthus occidentalis* and hereinafter referred to by the name 'SMCOSS'.

The new *Cephalanthus* plant is a product of a controlled breeding program conducted by the Inventor in Grand Haven, Mich. The objective of the breeding program is to create new compact and freely branching *Cephalanthus* plants with improved flowers and cold hardiness.

The new *Cephalanthus* plant originated from an open-pollination in 2005 in Grand Haven, Mich. of *Cephalanthus occidentalis* 'Britton Lake', not patented, as the female, or seed, parent with an unknown selection of *Cephalanthus occidentalis* as the male, or pollen, parent. The new *Cephalanthus* plant was discovered and selected by the Inventor in 2009 as a single flowering plant within the progeny of the stated open-pollination in a controlled environment in Grand Haven, Mich.

Asexual reproduction of the new *Cephalanthus* plant by softwood cuttings in a controlled environment in Grand Haven, Mich. since June, 2009 has shown that the unique features of this new *Cephalanthus* plant are stable and reproduced true to type in successive generations of asexual reproduction.

SUMMARY OF THE INVENTION

Plants of the new *Cephalanthus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMCOSS'.

These characteristics in combination distinguish 'SMCOSS' as a new and distinct *Cephalanthus* plant:

1. Compact, upright and mounded plant habit.
2. Vigorous growth habit.
3. Freely branching habit; dense and bushy habit.
4. Glossy green-colored leaves that develop anthocyanin in the spring and autumn.
5. Spherical head-type inflorescences with numerous white-colored flowers.
6. Red-colored fruits.
7. Good garden performance.

Plants of the new *Cephalanthus* can be compared to plants of the female parent, 'Britton Lake'. Plants of the new *Cephalanthus* differ from plants of 'Britton Lake' in the following characteristics:

1. Plants of the new *Cephalanthus* are more compact than plants of 'Britton Lake'.
2. Leaves of plants of the new *Cephalanthus* are glossy and develop anthocyanin in the spring and autumn whereas leaves of plants of 'Britton Lake' are not glossy and do not develop anthocyanin.
3. Plants of the new *Cephalanthus* and 'Britton Lake' differ in fruit color as plants of 'Britton Lake' have green-colored fruits.

Plants of the new *Cephalanthus* can be compared to plants of the *Cephalanthus occidentalis* 'Sputnik', not patented. In side-by-side comparisons conducted in Grand Haven, Mich., plants of the new *Cephalanthus* differed from plants of 'Sputnik' in the following characteristics:

1. Plants of the new *Cephalanthus* were much more compact than plants of 'Sputnik'.
2. Leaves of plants of the new *Cephalanthus* were glossy and developed anthocyanin in the spring and autumn whereas leaves of plants of 'Sputnik' were not glossy and did not develop anthocyanin.
3. Plants of the new *Cephalanthus* and 'Sputnik' differed in fruit color as plants of 'Sputnik' had green-colored fruits.

BRIEF DESCRIPTION OF THE PHOTOGRAPHS

The accompanying colored photographs illustrate the overall appearance of the new *Cephalanthus* plant showing the colors as true as it is reasonably possible to obtain in colored reproductions of this type. Colors in the photographs may differ slightly from the color values cited in the detailed botanical description which accurately describe the colors of the new *Cephalanthus* plant.

The photograph on the first sheet is a side perspective view of a typical plant of 'SMCOSS' grown in an outdoor nursery.

The photograph on the second sheet is a close-up view of a typical inflorescence of 'SMCOSS'.

The photograph on the third sheet is a close-up view of typical fruits of 'SMCOSS'.

DETAILED BOTANICAL DESCRIPTION

The aforementioned photographs and following observations, measurements and values describe plants grown during the summer and autumn in ground beds in an outdoor nursery in Grand Haven, Mich. and under cultural practices typical of commercial production. Plants were 3.5 years old when the photographs and the description were taken. In the description, color references are made to The Royal Horticultural Society Colour Chart, 1995 Edition, except where general terms of ordinary dictionary significance are used.

Botanical classification: *Cephalanthus occidentalis* 'SMCOSS'.

Parentage:

*Female, or seed, parent.*—*Cephalanthus occidentalis* 'Britton Lake', not patented.

*Male, or pollen, parent.*—Unknown selection of *Cephalanthus occidentalis*, not patented.

Propagation:

*Type.*—By softwood cuttings.

*Time to initiate roots, summer.*—About one month at 20° C.

*Time to produce a rooted young plant, summer.*—About eight months at 20° C.

*Root description.*—Medium in thickness; somewhat fibrous; white and brown in color.

*Rooting habit.*—Freely branching; dense.

Plant description:

*Plant and growth habit.*—Perennial shrub; compact, upright and mounded plant habit; vigorous growth habit.

*Branching habit.*—Freely branching habit with about 16 lateral branches developing per plant; pinching enhances lateral branch development.

*Plant height.*—About 47 cm.

*Plant diameter* (*area of spread*).—About 71 cm.

Lateral branch description:

*Length.*—About 40 cm.

*Diameter.*—About 3 mm.

*Internode length.*—About 3.8 cm.

*Texture.*—Slightly pubescent.

*Aspect.*—About 30° to 40° from vertical.

*Color.*—Close to 197A.

Leaf description:

*Arrangement.*—Opposite, simple.

*Length.*—About 8.5 cm.

*Width.*—About 3.8 cm.

*Shape.*—Lanceolate.

*Apex.*—Acuminate.

*Base.*—Obtuse.

*Margin.*—Entire.

*Texture and luster, upper surface.*—Smooth, glabrous; leathery; glossy.

*Texture and luster, lower surface.*—Pubescence along veins; leathery; matte.

*Venation pattern.*—Pinnate.

*Color.*—Developing leaves, upper surface: Close to 146B; anthocyanin, close to 59A. Developing leaves, lower surface: Close to 146B. Fully expanded leaves, upper surface: Close to 147A; venation, close to 160B; anthocyanin, close to 59A. Fully expanded leaves, lower surface: Close to 137B; venation, close to 160C.

*Petioles.*—Length: About 2 cm. Diameter: About 2 mm. Texture, upper and lower surfaces: Smooth, glabrous. Color, upper and lower surfaces: Close to 146C.

Flower description:

*Flower appearance and arrangement.*—Single tubular flowers arranged on dense terminal head-type inflorescences; heads spherical in shape; freely flowering habit with usually about 195 flowers per inflorescence; flowers face upright to outwardly depending on position on the head.

*Natural flowering season.*—Plants flower from July to August in Michigan; flowers not persistent.

*Fragrance.*—Slightly fragrant.

*Inflorescence height.*—About 2.5 cm.

*Inflorescence diameter.*—About 2.5 cm.

*Flower diameter.*—About 2 mm.

*Flower length* (*height*).—About 1.3 cm.

*Flower buds.*—Length: About 3 mm. Diameter: About 1 mm. Shape: Ovate. Color: Close to 144B.

*Petals.*—Quantity and arrangement: Four petals in a single tubular whorl. Length: About 3 mm. Width: About 2 mm. Apex: Acute. Margin: Entire. Texture, upper and lower surfaces: Smooth, glabrous. Color: When opening, upper and lower surfaces: Close to 155A. Fully opened, upper and lower surfaces: Close to 155A.

*Sepals.*—Quantity and arrangement: Four or five in a single whorl. Length: About 0.5 mm. Width: About 0.5 mm. Shape: Lanceolate. Apex: Acute. Base: Cuneate. Margin: Entire. Texture, upper and lower surfaces: Smooth, glabrous. Color: When opening, upper and lower surfaces: Close to 144C. Fully opened, upper and lower surfaces: Close to 144C.

*Peduncles.*—Length: About 4.5 cm. Diameter: About 2 mm. Strength: Strong. Texture: Smooth, glabrous. Color: Close to 145A.

*Pedicels.*—Length: About 4 cm. Diameter: About 2 mm to 3 mm. Strength: Strong. Texture: Smooth, glabrous. Color: Close to 145A.

*Reproductive organs.*—Androecium: Quantity per flower: About four. Anther size: About 1 mm by 2 mm. Anther shape: Oblong. Anther color: Close to 18B to 18C. Amount of pollen: Moderate. Pollen color: Close to 18B to 18C. Gynoecium: Quantity per flower: One. Pistil length: About 1.5 cm. Style length: About 1.2 cm. Style color: Close to 157D. Stigma appearance: Round. Stigma color: Close to 200C. Ovary color: Close to 157D.

*Fruits.*—Length: About 2 cm. Diameter: About 2 cm. Color: Close to 42B.

Garden performance: Plants of the new *Cephalanthus* have been observed to have good garden performance and to tolerate rain, wind and temperatures ranging from about −30° C. to about 40° C.

Pathogen & pest resistance: Plants of the new *Cephalanthus* have been observed to be resistant to leaf gall. Plants of the new *Cephalanthus* have not been shown to be resistant to pests and pathogens common to *Cephalanthus* plants.

It is claimed:

1. A new and distinct *Cephalanthus* plant named 'SMCOSS' as illustrated and described.

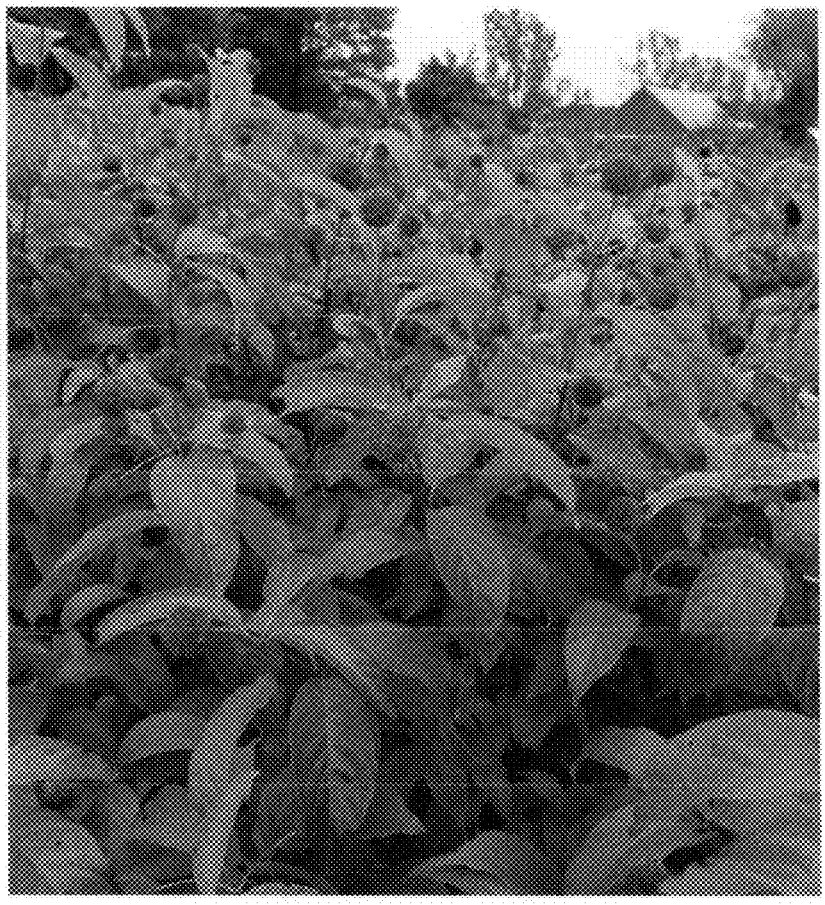

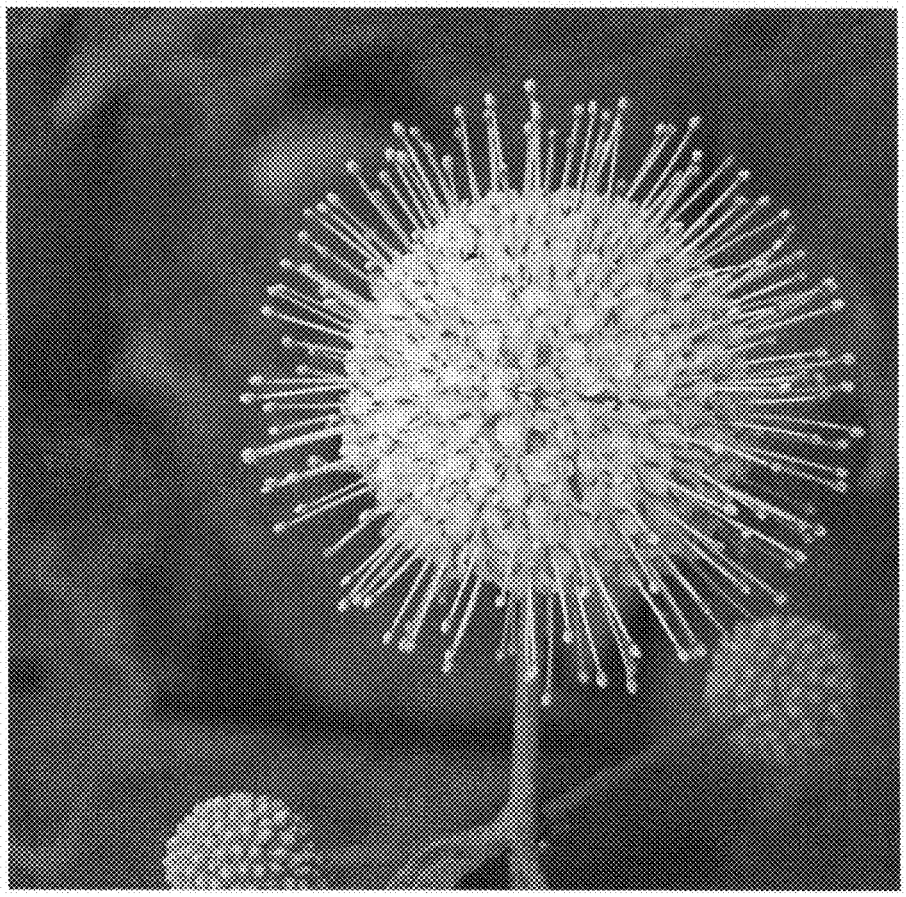

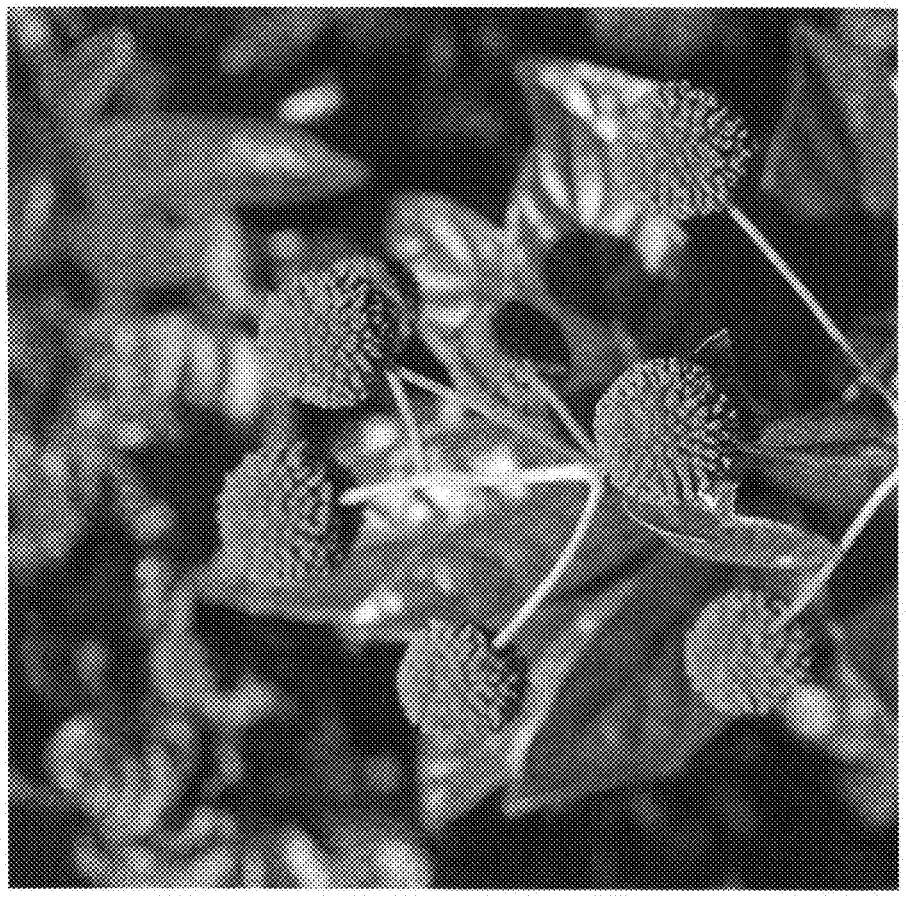

* * * * *